(12) United States Patent
Isizaka et al.

(10) Patent No.: US 9,320,684 B2
(45) Date of Patent: Apr. 26, 2016

(54) DENTAL RESTORATIVE MATERIAL

(75) Inventors: Nobuyuki Isizaka, Tokyo (JP); Tatsuya Yamazaki, Tokyo (JP); Junichiro Yamakawa, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 42 days.

(21) Appl. No.: 14/127,214

(22) PCT Filed: Jun. 22, 2012

(86) PCT No.: PCT/JP2012/065990
§ 371 (c)(1),
(2), (4) Date: Jan. 28, 2014

(87) PCT Pub. No.: WO2012/176877
PCT Pub. Date: Dec. 27, 2012

(65) Prior Publication Data
US 2014/0206792 A1    Jul. 24, 2014

(30) Foreign Application Priority Data
Jun. 24, 2011 (JP) ................................. 2011-140641

(51) Int. Cl.
*A61K 6/08* (2006.01)
*A61K 6/06* (2006.01)
*A61K 6/00* (2006.01)
*A61K 6/02* (2006.01)

(52) U.S. Cl.
CPC .............. *A61K 6/0681* (2013.01); *A61K 6/0005* (2013.01); *A61K 6/0008* (2013.01); *A61K 6/0011* (2013.01); *A61K 6/0073* (2013.01); *A61K 6/0091* (2013.01); *A61K 6/024* (2013.01); *A61K 6/08* (2013.01)

(58) Field of Classification Search
None
See application file for complete search history.

(56) References Cited

U.S. PATENT DOCUMENTS

| | | | | |
|---|---|---|---|---|
| 5,356,951 A * | 10/1994 | Yearn et al. | | 523/116 |
| 5,530,038 A * | 6/1996 | Yamamoto et al. | | 523/116 |
| 5,773,489 A * | 6/1998 | Sato | | 523/115 |
| 6,660,194 B1 * | 12/2003 | Arita | | 264/17 |
| 6,933,327 B2 * | 8/2005 | Yamakawa et al. | | 523/115 |
| 7,678,843 B2 * | 3/2010 | Fusejima et al. | | 523/117 |
| 2003/0036582 A1 * | 2/2003 | Yamakawa et al. | | 523/115 |
| 2008/0081848 A1 * | 4/2008 | Shih et al. | | 522/92 |
| 2008/0081849 A1 * | 4/2008 | Fusejima et al. | | 522/153 |
| 2009/0253825 A1 * | 10/2009 | Ohtsuka et al. | | 523/116 |
| 2010/0068678 A1 * | 3/2010 | Tanaka et al. | | 433/224 |
| 2011/0046260 A1 | 2/2011 | Okubayashi et al. | | |
| 2011/0257292 A1 | 10/2011 | Okubayashi et al. | | |
| 2012/0252654 A1 * | 10/2012 | Kariya et al. | | 501/134 |
| 2013/0096226 A1 | 4/2013 | Toriyabe et al. | | |

FOREIGN PATENT DOCUMENTS

| | | |
|---|---|---|
| JP | 9-169613 A | 6/1997 |
| JP | 9-255516 A | 9/1997 |
| WO | 02/15847 A1 | 2/2002 |
| WO | 2009/133913 A1 | 11/2009 |
| WO | 2011/074222 A1 | 6/2011 |
| WO | 2011/158742 A1 | 12/2011 |

OTHER PUBLICATIONS

International Search Report Dated Jul. 23, 2012, Mailed Jul. 31, 2012.
English Translation of International Search Report Dated Jul. 23, 2012, Mailed Jul. 31, 2012.
European Search Report dated Nov. 17, 2014.

* cited by examiner

*Primary Examiner* — Peter A Salamon
(74) *Attorney, Agent, or Firm* — Norris McLaughlin & Marcus PA

(57) ABSTRACT

The present invention discloses a dental restorative material comprising 10-50 mass % of (A) a polymerizable monomer, 5-80 mass % of (B) an organic-inorganic composite filler which is prepared by dispersing an inorganic fine filler having an average particle diameter of 1 μm or smaller in an organic matrix and has an average particle diameter of 5.0-50 μm, and 10-60 mass % of (C) a third component, i.e., an inorganic filler having an average particle diameter of 1.1-5.0 μm, wherein the absolute value of the difference between the refractive index [nC] of the inorganic filler (C) and the refractive index [nB] of the organic-inorganic composite filler (B) (i.e., |nC−nB|) is 0.005-0.07 at 32° C. and the absolute value of the difference between the refractive index [nA] of the cured product of the polymerizable monomer (A) and the refractive index [nC] of the inorganic filler (C) (i.e., |nA−nC|) is 0.005-0.05 at 32° C.

4 Claims, No Drawings

DENTAL RESTORATIVE MATERIAL

This application is a 371 application of PCT/JP2012/065990 filed Jun. 22, 2012, which claims foreign priority benefit under 35 U.S.C. §119 of Japanese application Nos. 2011-140641 filed Jun. 24, 2011.

TECHNICAL FIELD

The present invention relates to a dental restorative material superior in color conformability to tooth. The present dental restorative material is used suitably in applications such as dental material, dental restorative material for crown, CAD/CAM blocks and the like.

BACKGROUND ART

Dental restorative material can provide a color close to the natural tooth and is easily operated in the treatment of tooth. Therefore, it has rapidly come into wide use as a restorative material for the teeth having caries, etc. In recent years, it has been used in most cases of the treatment of anterior teeth. Recently, it has begun to be used in the restoration of, for example, posterior teeth upon which a high occlusional pressure is applied.

Dental restorative material is a high viscosity paste-like composition constituted mainly by a polymerizable monomer, a filler and a polymerization initiator. The filler has a great influence on the esthetic properties, mechanical properties and the like of the cured body of the dental restorative material, depending upon the composition, shape, particle diameter, use amount, etc. of the filler used. For example, when there is used an inorganic fine filer made of inorganic particles of 1 µm or smaller in average particle diameter and/or an agglomerate thereof, the resulting dental restorative material can have good wear resistance and surface smoothness/gloss.

However, the inorganic fine filler has a very large specific surface area and, therefore, a paste-like dental restorative material containing such an inorganic fine filler has a high stickiness before curing. In order to allow this dental restorative material to have a stickiness suitable for operation thereof, the use amount of monomer in the material need be increased. In this case, however, there occur problems that the handling property of the dental restorative material deteriorates, the polymerization shrinkage amount of the cured body thereof increases, and the mechanical strength of the cured body decreases.

In order to avoid the above problems while realizing the high surface smoothness/gloss and wear resistance which are features when the above-mentioned inorganic fine filler is used, it was found to use an organic-inorganic composite filler. The organic-inorganic composite filler is produced by mixing beforehand an inorganic fine filler and a polymerizable monomer, polymerizing and curing the mixture, and grinding the polymerized resin obtained. This organic-inorganic composite filler contains an inorganic fine filler and therefore the dental restorative material using the composite filler can give, when cured, high surface smoothness/gloss and wear resistance. Further, since the inorganic fine filler is dispersed in the organic matrix constituted by the cured polymerizable monomer, the paste-like dental restorative material before curing has no excessively high stickiness.

Even in the dental restorative material containing the Organic-inorganic composite filler, there is a case that the color of the cured body thereof is unable to match the color of tooth. In such a case, patients are not fully satisfied when high esthetics is required in their dental treatments. Specifically explaining, it is such a case that dental restoration is conducted by selecting a paste-like dental restorative material (not cured) fully matching the color and transparency of the tooth of patient but the cured body of the material does not match the color and transparency of the tooth of patient. That is, it is a case that, after the actual restoration of tooth, the cured body of the dental restorative material filled in tooth does not accurately match the color and texture of surrounding tooth. Further, it is a case that the boundary between the surrounding tooth and the cured body can be recognized visually.

Meanwhile, the optical properties of the dental restorative material include a light-diffusing property which has a great influence on the esthetics of tooth. Here, the light-diffusing property is such a property of translucent material that a light incident on a translucent material (e.g. cured body of dental restorative material) is diffused into various directions in the translucent material. The diffusion of incident light takes place because the incident light is refracted and reflected by the filler contained in the translucent material.

The reflected light appearing due to the diffusion of a light incident on a translucent material has a color of the translucent material and a color reflecting the color of the background thereof. Accordingly, a dental restorative material of higher light-diffusing property makes smaller the difference between the color of the cured body of the dental restorative material and the color of the background and makes vague the boundary between cured body and tooth. That is, the color conformability between tooth and cured body is higher.

As an indicator of the light-diffusing property, there was proposed the diffusion degree (D) represented by the following formula. With a larger diffusion degree (D) of translucent material, the light transmitted through the translucent material shows higher light-diffusing property.

$$D=\{(I_{20}/\cos 20°)+(I_{70}/\cos 70°)\}/(2\times I_0)$$

(in the above formula, $I_0$, $I_{20}$ and $I_{70}$ are, when a light is applied perpendicularly to the surface of a sheet-shaped sample of given thickness obtained by curing a dental restorative material, the intensities of lights transmitted through the sample in the directions of 0°, 20° and 70° relative to the incident direction of the light applied.)

Under the above background, there was proposed a dental restorative material wherein the diffusion degree (D) of the above-mentioned dental restorative material containing the organic-inorganic composite filler was enhanced (see Patent Literature 1). In this dental restorative material, the diffusion degree (D) is enhanced, whereby the color conformability between the cured body of the dental restorative material filled in the cavity of tooth, i.e. filled material and the surrounding tooth is improved.

In order to practically enhance the diffusion degree of the cured body of dental restorative material, the Patent Literature 1 proposes, in claim 3, compounding, in a dental restorative material, an organic-inorganic composite filler satisfying the following conditions (1) and (2).

(1) The average particle diameter is 1 to 20 µm.
(2) The absolute value of $n_F - n_M$ is 0.01 or larger. Here, $n_F$ is the refractive index of an organic-inorganic composite filler. $n_M$ is the refractive index of the matrix resin constituting the cured body of the dental restorative material In the Patent Literature 1, it is described that the dental restorative material may contain other inorganic filler (a third component inorganic filler) besides the organic-inorganic composite filler. Specifically, it is described that the dental restorative material contains fine spherical inorganic filler having an average particle diameter of 1 µm or smaller. The main purpose of adding this filler is to make easier the filling operation of uncured paste-like dental restorative material ([0020]). It is also described that other purpose is to allow the spherical inorganic filler to function as a controlling agent of the refractive index of matrix portion, to satisfy the above condition (2) for the organic-inorganic composite filler ([0065]). This fine spherical inorganic filler, however, has an average particle diameter close to the wavelength (0.4 to 0.7 µm) of visible light; therefore, the change of the refractive index of the matrix portion by the spherical inorganic filler is very small. That is, the influence on the diffusion degree of cured body is small when such a fine spherical inorganic filler is compounded in the dental restorative material.

PRIOR ART LITERATURE

Patent Literature

Patent Literature 1: JP 2002-138008 A

SUMMARY OF THE INVENTION

Task to be Achieved by the Invention

The present inventors produced a dental restorative material having a diffusion degree of 0.01 or higher by using, as an organic-inorganic composite filler, a filler satisfying the above-mentioned conditions (1) and (2), and investigated the color conformability of the cured body of the dental restorative material. As a result, it was found that the cured body of the restorative material had fairly good color conformability to surrounding tooth. However, as seen in Examples, the diffusion degree itself of the cured body was not sufficiently high. That is, the above dental restorative material was insufficient in color conformability.

Hence, the task of the present invention is to provide a dental restorative material containing an organic-inorganic composite filler, which is superior in wear resistance, surface smoothness and gloss, easiness of handling, mechanical strength, etc. and which is highly improved in color conformability between the cured body thereof and surrounding tooth.

Means for Achieving the Task

In view of the above task, the present inventors continued the study. As a result, the present inventors thought of allowing the third component inorganic filler used together with the organic-inorganic composite filler, to have a relatively large average particle diameter of 1.1 to 5.0 µm. The present inventors further thought of controlling the refractive index of the third component inorganic filler, the refractive index of the organic-inorganic composite filler and the refractive index of the organic matrix resin in the cured body of the dental refractive material, in particular ranges. The present inventors found that, by adopting the Above-mentioned constitution, a dental restorative material having good color conformability to surrounding tooth could be obtained. The finding has led to the completion of the present invention.

The present invention is a dental restorative material comprising:

10 to 50 mass % of (A) a polymerizable monomer, 5 to 80 mass % of (B) an organic-inorganic composite filler having an average particle diameter of 5.0 to 50 µm, which comprising an inorganic fine filler having an average particle diameter of 1 µm or smaller and an organic matrix dispersing the inorganic fine filler therein, and 10 to 60 mass % of (C) a third component, i.e. an inorganic filler having an average particle diameter of 1.1 to 5.0 µm, wherein the absolute value |nC−nB| of the difference between the refractive index [nC] of the inorganic filler (C) at 32° C. and the refractive index [nB] of the organic-inorganic composite filler (B) at 32° C. is 0.005 to 0.07, and the absolute value |nA−nC| of the difference between the refractive index [nA] of the cured body of the polymerizable monomer (A) at 32° C. and the refractive index [nC] of the inorganic filler (C) at 32° C. is 0.005 to 0.05.

Effect of the Invention

The present dental restorative material contains the organic-inorganic composite filler and the third component inorganic filler each in a sufficient amount. Therefore, the present dental restorative material is superior in easiness of handling in the treatment of tooth. Further, the cured body of the present dental restorative material is superior in mechanical strength, surface smoothness and gloss, and wear resistance.

The third component inorganic filler has a relatively large average particle diameter of 1.1 to 5.0 µm. Further, the difference between the refractive index of the third component inorganic filler and the refractive index of the organic inorganic composite filler is controlled in a particular range. Furthermore, the difference between the refractive index of the third component inorganic filler and the refractive index of the cured resin of the polymerized monomer used in the dental restorative material is controlled in a particular range. Accordingly, the cured body of the dental restorative material has an extremely large diffusion degree (D) due to the reasons considered as below. As a result, when the dental restorative material is used, for example, in the treatment of tooth, the cured body obtained by filling the dental restorative material in a tooth and curing the material, i.e. filled material shows a strikingly high color conformability to surrounding tooth.

That is, the relatively large average particle diameter of the third component inorganic filler is larger than the wavelength of visible light range. Accordingly, the optical property of the cured body of the dental restorative material containing a large amount of the third component inorganic filler is greatly influenced by the refractive index [nC] of the third component inorganic filler. In the present dental restorative material, the refractive index [nC] of the third component inorganic filler (C) and the refractive index [nB] of the organic-inorganic composite filler (B) are controlled so that the absolute value of the difference between them, i.e. |nC−nB| becomes 0.005 to 0.07.

Meanwhile, in the cured body of the dental restorative material containing the third component inorganic filler in a large mount as mentioned above, the organic-inorganic composite filler (B) are surrounded by a large amount of the third component inorganic filler.

As mentioned above, the refractive index of the third component inorganic filler surrounding the organic-inorganic composite filler is significantly different from the refractive index of the organic-inorganic composite filler. Accordingly, a light incident on the cured body of the dental restorative material is refracted and reflected largely in the interface between the organic-inorganic composite filler and the third component inorganic filler. This refraction and reflection increases the diffusion degree (D) of the cured body of the dental restorative material.

In addition, in the present dental restorative material, the refractive index [nC] of the third component inorganic filler (C) and the refractive index [nA] of the cured resin of the polymerizable monomer (A) (the cured resin is the matrix of the the cured body in which the filler is dispersed) are controlled so that the absolute value of the difference between the two refractive indices, i.e. |nA−nC| becomes 0.005 to 0.05.

Accordingly, a light incident on the cured body is refracted and reflected largely in the interface between the third component inorganic filler and the matrix. As a result, in the cured body of the present dental restorative material, there is, in addition to the refraction and reflection at the interface between the organic-inorganic composite filler and the third component inorganic filler, the refraction and reflection at the interface between the third component inorganic filler and the matrix of the cured body, whereby the diffusion degree of the cured body is increased further.

Further, at the interface between the organic-inorganic composite filler and the third component inorganic filler surrounding the composite filer, there take place repeatedly the refraction and reflection at the interface between the third component inorganic filler and the matrix of the cured body and the refraction and reflection at the interface between the organic-inorganic composite filler and the third component inorganic filler, in extremely close domains. Owing to these refractions and reflections, a light incident on the cured body is diffused into various directions in a complicated pattern. Due to the above-mentioned reasons, the increasing effect of diffusion degree of cured body is sufficiently promoted.

MODE FOR CARRYING OUT THE INVENTION

The dental restorative material of the present invention contains at least (A) a polymerizable monomer, (B) an organic-inorganic composite material and (C) an inorganic filler.

The present dental restorative material may contain, besides the above-mentioned components, a polymerization initiator and optional additives such as coloring material, stabilizer and the like. The present dental restorative material containing these components is relatively viscous and paste-like. The present dental restorative material is filled in, for example, the cavity of tooth, polymerized and cured. The cured body obtained contains at least an organic matrix portion which is a cured resin formed by the polymerization of the polymerizable monomer (A), the organic-inorganic composite filler (B) and the third component inorganic filler (C) dispersed in the organic matrix portion. This cured body enables restoration of, for example, the cavity of tooth.

Description is made on each of the above-mentioned components.

<Polymerizable Monomer (A)>

In the present invention, the polymerizable monomer (A) may be any known polymerizable monomer usable in the production of dental restorative material. The cured resin formed by the curing of the polymerizable monomer (A) has a refractive index at 32° C. of preferably 1.45 to 1.65, more preferably 1.50 to 1.60, in consideration of the color conformability between tooth and the cured body of dental restorative material.

Examples of the polymerizable monomer are monomers A to D shown below.

A Monofunctional Vinyl Monomers

Methacrylates such as methyl methacrylate, ethyl methacrylate, isopropyl methacrylate, hydroxyethyl methacrylate, tetrahydrofurfuryl methacrylate, glycidyl methacrylate and the like; acrylates corresponding to the above methacrylates; etc.

Acrylic acid, methacrylic acid, p-methacryloyloxybenzoic acid, N-2-hydroxy-3-methacryloyloxypropyl-N-phenylglycine, 4-methacyloyloxyethyltrimellitic acid, anhydrides thereof, 6-methacryloyloxyhexamethylenemalonic acid, 10-methacryloyloxydecamethylenemalonic acid, 2-methacryloyloxyethyl dihydrogen phosphate, 10-methacryloyloxydecamethylene dihydrogen phosphate, 2-hydroxyethyl hydrogen phenyl phosphate, etc.

B Bifunctional Vinyl Monomers

B-1 Aromatic Compound Type Monomers 2,2-Bis(methacryloyloxyphenyl)propane, 2,2-bis[4-(3-methacryloyloxy)-2-hydroxypropoxyphenyl]propane (hereinafter abbreviated as bis-GMA), 2,2-bis(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxydiethoxyphenyl)propane, 2(4-methacryloyloxydiethoxyphenyl)-2(4-methacryloyloxyditriethoxyphenyl)propane, 2(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane; acrylates corresponding to these methacrylates; etc.

Diadducts obtained by addition reaction between —OH group-containing vinyl monomer [e.g. methacrylate (e.g. 2-hydroxyethyl methacrylate, 2-hydroxypropyl methacrylate or 3-chloro-2-hydroxypropyl methacrylate) or acrylate corresponding to the methacrylate] and aromatic group-containing diisocyanate compound (e.g. diisocyanato methylbenzene or 4,4'-diphenylmethane diisocyanate); etc.

B-2 Aliphatic Compounds

Ethylene glycol dimethacrylate, diethylene glycol dimethacrylate, triethylene glycol dimethacrylate (hereinafter abbreviated as 3G), butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate; acrylates corresponding to these methacrylates; etc.

Diadducts obtained by addition reaction between —OH group-containing vinyl monomer [e.g. methacrylate (e.g. 2-hydroxyethyl methacrylate, 2-hydroxypropyl methacrylate or 3-chloro-2-hydroxypropyl methacrylate) or acrylate corresponding to the methacrylate] and diisocyanate compound [e.g. hexamethylene diisocyanate, trimethylhexamethylene diisocyanate, diisocyanato methylcyclohexane, isophorone diisocyanate, or methylenebis(4-cyclohexyl isocyanate)]; etc.

Acrylic anhydride, methacrylic anhydride, 1,2-bis(3-methacryloyloxy-2-hydroxypropoxy)ethyl, di(2-methacryloyloxypropyl)phosphate, etc.

C Trifunctional Vinyl Monomers

Methacrylates such as trimethylolpropane trimethacrylate, trimethylolethane trimethacrylate, pentaerythritol trimethacrylate, trimethylolmethane trimethacrylate and the like; acrylates corresponding to these methacrylates; etc.

D Tetrafunctional Vinyl Monomers

Pentaerythritol tetra-methacrylate, pentaerythritol tetraacrylate; or diadducts obtained by the addition between diisocyanate compound [e.g. diisocyanato methylbenzene, diisocyanato methylcyclohexane, isophorone diisocyanate, hexamethylene diisocyanate, trimethylhexamethylene diisocyanate, methylene-bis(4-cyclohexyl isocyanate), 4,4-diphenylmethane diisocyanate, or tolylene-2,4-diisocyanate]and glycidol dimethacrylate; etc.

Of the above-mentioned polymerizable monomers, preferred are acryloyl group- or methacryloyl group-containing polymerizable monomers because they give a cured resin having good mechanical strength, good biocompatibility, etc. These polymerizable monomers are highly polymerizable and the cured bodies thereof have appropriately high mechanical properties. These polymerizable monomers are used preferably in a combination of 90 mass % or more, preferably 92 to 98 mass % of a bifunctional vinyl monomer as a main component and 10 mass % or less, preferably 2 to 8 mass % of a monofunctional vinyl monomer or a polyfunctional (at least trifunctional) vinyl monomer. By controlling the proportions of the monomers used, in the above ranges, the cured resin obtained can have controlled properties.

In the present invention, the use amount of the polymerizable monomer (A) is 10 to 50 mass % relative to the total mass of the polymerizable monomer (A), the organic-inorganic composite filler (B) and the inorganic filler (C), which are all the essential components of the present dental restorative material.

When the use amount of the polymerizable monomer (A) is smaller than 10 mass %, the dispersibility of the organic-inorganic composite filler and the inorganic filler is insufficient. As a result, the paste-like dental restorative material is not easy to operate and the cured body thereof has a low mechanical strength. Meanwhile, when the use amount of the polymerizable monomer (A) is larger than 50 mass %, the use amounts of the organic-inorganic composite filler and the inorganic filler are insufficient, and the paste-like dental restorative material is not easy to operate and the cured body thereof has a low mechanical strength. Further, the cured body has low surface smoothness and gloss and low wear resistance. In view of these matters, the use amount of the polymerizable monomer (A) is preferably 15 to 43 mass %.

<Organic-Inorganic Composite Filler (B)>

In the present invention, the organic-inorganic composite filler is defined as a composite filler obtained by dispersing an inorganic fine filler in an organic matrix (resin). The organic-inorganic composite filler can be produced, for example, by dispersing an inorganic fine filler in a polymerizable monomer to obtain a curable composition, polymerizing and curing the curable composition to obtain a polymer resin, and grinding the polymer resin. The inorganic fine filler dispersed in the organic matrix has an average particle diameter of 1.0 µm or smaller, preferably 0.05 to 1.0 µm, more preferably 0.1 to 0.5 µm. The organic-inorganic composite filler has an average particle diameter of 5.0 to 50 µm, preferably 8 to 20 µm.

The inorganic fine filler dispersed in the organic matrix has an average particle diameter of 1.0 µm or smaller; therefore, each gap between the filler particles is small. As a result, the portion constituted by the polymer alone, present in the gap is small. The portion constituted by the polymer alone causes breakage easily. Accordingly, the organic-inorganic composite filler of the present invention can avoid a reduction in mechanical strength. Further, the organic-inorganic composite filler obtained has good wear resistance and good surface smoothness and gloss. Meanwhile, the inorganic filler has an average particle diameter of 0.05 µm or larger and therefore has no high agglomeration tendency between the particles. Accordingly, the polymerizable monomer can easily infiltrate uniformly into the inorganic fine filler, when producing the organic-inorganic composite filler. As a result, the organic-inorganic composite filler obtained is improved in uniformity of refractive index.

An organic-inorganic composite filler having a non-uniform refractive index is low in light-diffusing property. In this case, the color conformability between the cured body of dental restorative material and tooth is low.

When the organic-inorganic composite filler is produced in a state that the polymerizable monomer is infiltrated into between the inorganic filler non-uniformly, the dental restorative material obtained gives a cured body low in mechanical strength. Further, the cured body is unable to exhibit sufficient wear resistance and sufficient surface smoothness and gloss. From these standpoints, the inorganic fine filler dispersed in the organic matrix is preferred to have an average particle diameter of 0.1 to 0.5 µm.

The organic-inorganic composite filler having an average particle diameter of the above range has an appropriate specific surface area. As a result, reflection and refraction of light can take place actively in the cured body of the dental restorative material using the composite filler, and the cured body can show a high diffusion degree. Further, since the organic-inorganic composite filler has an average particle diameter of 50 µm or smaller, the paste-like dental restorative material produced using the composite filler is free from poor operation such as poor unity or stickiness. Furthermore, the cured body thereof causes no problem such as deterioration of mechanical strength. From these standpoints, the organic-inorganic composite filler is preferred to have an average particle diameter of 8 to 20 µm.

In the organic-inorganic composite filler, the average particle diameter of the inorganic fine filler dispersed in the organic matrix (polymerized resin) can be measured using a scanning electron microscope. In the measurement, first the microphotograph of the inorganic fine filler is taken and then each diameter of the particles of the inorganic fine filler is measured. In the diameter measurement, each of at least 100 particles (randomly selected) of the inorganic fine filler is measured for diameter (circle-equivalent diameter) and the average particle diameter of the inorganic fine filler is calculated using the following formula.

Average particle diameter: [Mathematical expression 1]

$$X = \sqrt[3]{\frac{\sum_{i=1}^{n} X_i^3}{n}} \text{ (average volume diameter)}$$

$n$: Number of observed particles $x_i$: Particle diameter of $ith$ particle

The average particle diameter of the organic-inorganic composite filler is a median diameter obtained by measuring the particle size distribution of the composite filler according to the laser diffraction-scattering method and making calculation using the data. The sample used in the measurement is a dispersion obtained by dispersing 0.1 g of an organic-inorganic composite filler uniformly in 10 ml of ethanol.

In the organic-inorganic composite filler, the amount of the inorganic fine filler dispersed in the organic matrix is preferably 50 to 90 mass % (organic matrix: 50 to 10 mass %), more preferably 70 to 85 mass %. With this amount of the inorganic fine filler, the mechanical strength and refractive index of the organic-inorganic composite filler can be controlled at preferred levels.

Here, it is important that the absolute value |nC−nB| of the difference between the refractive index of the third component inorganic filler (C) at 32° C. and the refractive index of the organic-inorganic composite filler at 32° C. is 0.005 to 0.07. When there is used an organic-inorganic composite filler having a difference |nC−nB| of smaller than 0.005, the dental restorative material obtained, when cured, shows a low diffusion degree and gives low color conformability to surrounding tooth. Meanwhile, when there is used an organic-inorganic composite filler having a difference |nC−nB| of larger than 0.07, the dental restorative material obtained, when cured, is highly opaque and gives low color conformability to surrounding tooth.

(nC−nB) is preferred to be positive (plus) for higher diffusion degree of the cured body. (nC−nB) is more preferred to be 0.01 to 0.03 in order to allow the cured body to have a strikingly high diffusion degree, secure transparency, and have very high color conformability.

The reason therefor is not clarified but is presumed to be as follows. When |nC−nB| is larger than 0.005, reflection and refraction of light occur in the vicinity of the surface of the organic-inorganic composite filler, causing diffusion of light. When the refractive index difference (nC−nB) is negative, reflection of light occurs in the vicinity of the surface of the organic-inorganic composite filler, and the light incident into the organic-inorganic composite filler is refracted to be converged owing to the refractive index difference.

In contrast, when (nC−nB) is positive, reflection of light occurs in the vicinity of the surface of the organic-inorganic composite filler, and the light incident into the organic-inorganic composite filler is refracted to be diverged owing to the refractive index difference. In this case, since the light is refracted and diverged, the cured body of the dental restorative material shows very high light diffusivity.

In the organic-inorganic composite filler, the matrix portion thereof is formed by polymerization of polymerizable monomer. As the polymerizable monomer, there can be used the same polymerizable monomers as previously mentioned as the component (A), singly or in combination of a plurality of kinds.

As to the material of the inorganic fine filler dispersed in the organic-inorganic composite filler, there is no particular restriction as long as the material satisfies the above-mentioned requirement of |nC−nB|. As the material, there can be mentioned inorganic compounds such as metal oxide (e.g. amorphous silica or alumina); compound oxide containing silica and an oxide of metal selected from metals of groups I, II, III and IV of periodic table (preferably, silica-zirconia, silica-titania, silica-titania-barium oxide or the like); glass (e.g. borosilicate glass or fluoroaluminosilicate glass); and metal fluoride (e.g. ytterbium fluoride or yttrium fluoride).

Of these materials, particularly preferred are compound oxides composed mainly of silica and zirconia, because they can give radiopacity and high wear resistance to a cured body. The method for producing such an inorganic fine filler is not particularly restricted but is preferably a so-called sol-gel method. In the sol-gel method, an inorganic fine filler which is spherical or approximately spherical in shape and monodisperse, can be produced industrially and advantageously. Further in the sol-gel method, it is easy to allow the inorganic fine filler to have controlled refractive index and radiopacity.

In the sol-gel method, there is first prepared a solution of hydrolyzable organic silicon compound or a mixed solution of this compound and a hydrolyzable other organic metal compound. Then, the solution is added to an alkaline solvent which dissolves the organic metal compound but does not substantially dissolve the reaction product, to allow a hydrolysis reaction to proceed. With the progress of the hydrolysis reaction, a reaction product deposits. Thereafter, the deposit is isolated and dried.

In order to improve the dispersibility in the polymerizable monomer which later becomes the matrix portion of the organic-inorganic composite filler, it is preferred that the surface of the inorganic fine filler is subjected to a treatment for hydrophobing. There is no particular restriction to the treatment for hydrophobing, and a known treatment method can be adopted with no restriction. As an example of the representative treatment method for hydrophobing, there can be mentioned a method of dispersing and mixing an inorganic fine filler and a silane coupling agent (a hydrophobing agent) in an appropriate solvent using a ball mill or the like, then drying with an evaporator or a spray drier, and heating the resulting mixture at 50 to 150° C. As the silane coupling agent, there can be mentioned, for example, organosilicon compounds such as γ-methacryloyloxyalkyltrimethoxysilane, hexamethyldisilazane and the like.

There can further be mentioned a method of heating and refluxing an inorganic fine filler and the above-mentioned hydrophobing agent, for about several hours in the presence of a solvent such as alcohol. There can furthermore be mentioned, for example, a method using a titanate type coupling agent and a method of graft-polymerizing the above-mentioned polymerizable monomer on the surface of an inorganic fine filler.

As to the use amount of the hydrophobing agent, there is no particular restriction. The optimum use amount of the hydrophobing agent may be determined by beforehand confirming, by a test, the mechanical properties, etc. of the cured body of the dental restorative material obtained. The use amount is generally 1 to 30 mass parts relative to 100 mass parts of the inorganic fine filler.

The inorganic fine filler may be used in the form of a mixture of several kinds different in particle size distribution and kind of material.

In producing the organic-inorganic composite filler, a curable composition containing a polymerizable monomer and an inorganic fine filler is cured. Curing of the curable composition is ordinarily conducted by polymerizing the polymerizable monomer using a polymerization initiator. The kind and use amount of the polymerization initiator used are the same as those of the later-described polymerization initiator which is ordinarily used in curing the present dental restorative material. The curable composition may contain optional additives such as polymerization inhibitor, ultraviolet absorber, fluorescent agent, polymerization co-catalyst, pigment and the like.

The curable composition containing the above polymerizable monomer and the inorganic fine filler is cured and the polymer obtained is ground to obtain an organic-inorganic composite filler. In grinding the polymer, a ball mill, a vibration mill, a jet mill or the like is used preferably. The ground material is classified so as to have a desired particle diameter, by sieving, air classifier, water elutriation, or the like.

As the organic-inorganic composite filler, an organic-inorganic composite filler obtained by the method shown in Japanese patent Application 2011-005207 can also be used suitably. In this method, an organic-inorganic composite filler is produced by diluting an effective amount of a polymerization initiator and a polymerizable monomer with an organic solvent to prepare a diluted solution, immersing agglomerated particles of an inorganic fine filler in the diluted solution, then removing the organic solvent from the agglomerated particles, thereafter polymerizing and curing the polymerizable monomer to obtain a polymer, and grinding the polymer as necessary.

In the organic-inorganic composite filler obtained by the above method, agglomeration gaps of particular pore volume are formed between the particles of the inorganic fine filler. In the dental restorative material using the organic-inorganic composite filler produced by the above method, a large amount of a polymerizable monomer is present in the agglomeration gaps between the particles of the inorganic fine filler. Accordingly, in the cured body of the dental restorative material obtained using the organic-inorganic composite filler, a polymer of the polymerizable monomer is present in the agglomeration gaps between the particles of the inorganic fine filler. As a result, a mechanical interlocking force arises at the interfaces of the inorganic fine filler, and breakage hardly occurs at the interfaces of the organic-inorganic composite filler. Therefore, the cured body of the dental restorative material obtained can have a higher mechanical strength.

The organic-inorganic composite filler may be subjected, before being used in the dental restorative material, to washing, decolorization, surface treatment, etc. As an example of the decolorization method, there can be generally mentioned a method of dispersing the organic-inorganic composite filler in an appropriate solvent, dissolving a peroxide in the dispersion, stirring and, as necessary, heating. The peroxide may be any known peroxide.

The surface treatment is conducted according to the above-mentioned surface treatment method for inorganic fine filler.

In the dental restorative material of the present invention, the use amount of the organic-inorganic composite filler (B) is 5 to 80 mass %, preferably 7 to 50 mass % relative to the total mass of the polymerizable monomer (A), the organic-inorganic composite filler (B), and the inorganic filler (C), which are all the essential components of the present dental restorative material. When the use amount of the organic-inorganic composite filler (B) is smaller than 5 mass % or larger than 80 mass %, the cured body of the dental restorative material obtained has low color conformability to surrounding tooth and insufficient mechanical strength.

<Third Component Inorganic Filler (C)>

In the present dental restorative material, there is used, as a filler component other than the organic-inorganic composite filler (B), an inorganic filler (C) having an average particle diameter of 1.1 to 5.0 μm, preferably 1.5 to 3.0 μm. The average particle diameter of the third component inorganic filler is 1.1 μm or larger. Since this particle diameter is longer than the wavelength of visible light range, diffusion degree (D) of the cured body of the dental restorative material increases reliably. As a result, the cured body has high color conformability to surrounding tooth.

Meanwhile, the average particle diameter of the third component inorganic filler is 5.0 μm or smaller. Accordingly, the cured body has good wear resistance. Also, with this average particle diameter of 5.0 μm or smaller, the third component inorganic filler can surround the organic-inorganic composite filler in a favorable disposition. As a result, refraction and reflection of light can take place actively at the interface between the organic-inorganic composite filler and the third component inorganic filler.

In the present invention, as mentioned above, the absolute value |nC−nB| of the difference between the refractive index of the third component inorganic filler at 32° C. and the refractive index of the organic-inorganic composite filler (B) at 32° C. is 0.005 to 0.07. Further, the absolute value |nA−nC| of the difference between the refractive index of the third component inorganic filler at 32° C. and the refractive index [nA] of the cured resin of the polymerizable monomer (A) at 32° C. is 0.005 to 0.05.

When the |nA−nC| is smaller than 0.005, the cured body of the dental restorative material shows no high diffusion degree. As a result, the cured body has low color conformability to surrounding tooth. Meanwhile, when the |nA−nC| is larger than 0.05, opacity of the cured body of the dental restorative material increases. As a result, the cured body has low color conformability to surrounding tooth. |nA−nC| is preferably 0.01 to 0.03 in order to obtain higher diffusion degree and superior color conformability.

The value (nA−nC) obtained by subtracting the refractive index [nC] of the third component inorganic filler (C) from the refractive index [nA] of the cured resin of the polymerizable monomer (A) is preferred to be positive (plus) in order to obtain an even higher diffusion degree. The reason is the same as in the above-mentioned relation between the refractive index of the third component inorganic filler (C) and the refractive index of the organic-inorganic composite filler (B).

The material of the third component inorganic filler is selected from the same materials of the inorganic fine filler dispersed in the organic-inorganic composite filler. Also, the surface of the third component inorganic filler is preferably subjected to a surface treatment for hydrophobing, for dispersibility improvement. The treatment for hydrophobing is conducted in the same treatment method as adopted for the inorganic fine filler dispersed in the organic-inorganic composite filler.

In the present dental restorative material, the use amount of the third component inorganic filler (C) is 10 to 60 mass %, preferably 20 to 50 mass % relative to the total mass of the polymerizable monomer (A), the organic-inorganic composite filler (B), and the inorganic filler (C), which are all the essential components of the dental restorative material. With a use amount of the third component inorganic filler (C) of smaller than 10 mass %, effect of the cured body of the dental restorative material obtained is low in diffusion degree (D). As a result, the cured body shows insufficient color conformability to surrounding tooth. Meanwhile, With a use amount of the third component inorganic filler (C) of larger than 60 mass %, the paste-like dental restorative material obtained shows inferior handling property and the cured body thereof is low in surface smoothness and gloss and wear resistance, in treatment of tooth.

<Control of |nC−nB| and |nA−nC|>

In the present dental restorative material, as mentioned above, |nC−nB| is controlled at 0.005 to 0.07 and |nA−nC| is controlled at 0.005 to 0.05. Here, the refractive index (nC) of the third component inorganic filler (C) can be varied by selecting the material thereof. In general, the refractive indexes of inorganic fillers made of the materials mentioned previously are in range of 1.40 to 1.70, preferably 1.50 to 1.60. Accordingly, the refractive index of the third component inorganic filler can be controlled by selecting the material thereof.

The refractive index (nA) of the cured resin of the polymerizable monomer (A) can be varied by selecting the kinds of polymerizable monomers and the combination of polymerizable monomers. As mentioned above, the polymerizable monomer is selected from polymerizable monomers which give a cured resin having a refractive index of ordinarily 1.45 to 1.65, preferably 1.50 to 1.60, in view of the conformability to surrounding tooth.

The refractive index (nB) of the organic-inorganic composite filler (B) can be varied by the selection of the kind of the polymerizable monomer which is a raw material for organic matrix portion, the selection of the material of the inorganic fine filler dispersed in the organic matrix portion, and the content of the inorganic fine filler dispersed in the organic matrix portion. The refractive index (nB) of the organic-inorganic composite filler can be selected in a range of ordinarily 1.45 to 1.65, preferably 1.50 to 1.60.

<Polymerization Initiator>

The dental restorative material of the present invention can be cured without using any polymerization initiator when the polymerization is conducted by heating or the like. However, a polymerization initiator is used ordinarily in order to cure the polymerizable monomer (A). The polymerization initiator may be any known one and may be appropriately selected depending upon the polymerization method of the polymerizable monomer. The polymerization method includes, other than the above-mentioned heating method, a method of using a light energy such as ultraviolet light, visible light or the like, a method of using a reaction between a peroxide and an accelerator.

As the polymerization initiator using a reaction caused by a light energy (this reaction is hereinafter called photopolymerization), there can be used, for example, benzoin alkyl ethers such as benzoin methyl ether, benzoin ethyl ether, benzoin isopropyl ether and the like; benzyl ketals such as benzyl dimethyl ketal, benzyl diethyl ketal and the like; benzophenones such as benzophenone, 4,4'-dimethylbenzophenone, 4-methacryloxybenzophenone and the like; α-diketones such as diacetyl, 2,3-pentadione benzyl, camphor quinone, 9,10-phenanthraquinone, 9,10-anthraquinone and the like; thioxanthone compounds such as 2,4-diethoxythioxanthone, 2-chlorothioxanthone, methylthioxanthone and the like; and bisacylphosphine oxides such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis(2,4,6-trimethylbenzoyl)-phenylphosphine oxide and the like.

Incidentally, a reductant is often added to the photopolymerization initiator. As examples of the reducing agent, there can be mentioned tertiary amines such as 2-(dimethylamino) ethyl methacrylate, ethyl 4-dimethylaminobenzoate, N-methyldiethanolamine and the like; aldehydes such as laurylaldehyde, dimethylaminobenzaldehyde, terephthalaldehyde and the like; and sulfur-containing compounds such as 2-mercaptobenzoxazole, 1-decanethiol, thiosalicylic acid, thiobenzoic acid and the like.

As the polymerization initiator usable in thermal polymerization, there can be mentioned, for example, peroxides such as benzoyl peroxide, p-chlorobenzoyl peroxide, tert-butyl peroxy-2-ethylhexanoate, tert-butyl peroxydicarbonate, diisopropyl peroxydicarbonate and the like; azo compounds such as azobisisobutyronitrile and the like; boron compounds such as tributylborane, partial oxidation product of tributylborane, sodium tetraphenylborate, sodium tetrakis(p-fluorophenyl)borate, triethanolamine salt of tetraphenylboric acid and the like; and barbituric acids such as 5-butylbarbituric acid, 1-benzyl-5-phenylbarbituric acid and the like; sulfinic acid salts such as sodium benzenesulfinate, sodium p-toluenesulfinate and the like.

In the present invention, the use amount of the polymerization initiator is an effective amount known in the industry. It is generally 0.01 to 1 mass % relative to the total composition of dental restorative material containing optional additives.

<Optional Additives>

The dental restorative material of the present invention may contain an inorganic fine filler having an average particle diameter smaller than that of the third component inorganic filler (C), preferably of 0.05 to 0.5 µm. The purpose of adding this inorganic fine filler is to allow the paste-like dental restorative material to be improved in filling operation and the cured body thereof to have higher strength, controlled refractive index, etc. There is no particular restriction as to the shape of this inorganic fine filler which is an optional additive. The inorganic fine filler is preferably a spherical or approximately spherical inorganic fine filler and/or an agglomerate thereof in order to obtain high surface smoothness and gloss and high wear resistance. The use amount of the inorganic fine filler is 40 mass % or smaller, preferably 10 to 30 mass %, more preferably 10 to 20 mass % relative to the total composition of the dental restorative material containing optional additives.

The present dental restorative material may also contain known additives as long as they do not strikingly impair the effect of the dental restorative material. Ordinarily, there are added, in particular, small amounts of a white pigment (e.g. titanium oxide) and other organic or inorganic pigment in order to give a color of tooth. As other additives, a polymerization inhibitor, an ultraviolet absorber, etc. are added appropriately.

<Diffusion Degree (D) of Cured Body of Dental Restorative Material>

As mentioned above, the cured body of the dental restorative material of the present invention is high in diffusion degree (D) represented by the following formula and has high color conformability to surrounding tooth.

$$D=\{(I_{20}/\cos 20°)+(I_{70}/\cos 70°)\}/(2 \times I_0)$$

(in the above formula, $I_0$, $I_{20}$ and $I_{70}$ are, when a light is applied perpendicularly to the surface of a sheet-shaped sample, the intensities of lights transmitted by the sample in the directions of 0°, 20° and 70° relative to the incident direction of the light applied. The sheet-shaped sample is obtained by curing a dental restorative material into a sheet shape of 0.5 mm in thickness.)

Incidentally, in the measurement of the diffusion degree (D), the intensities of lights can be measured easily using a gonio-photometer. Trigonometric function (cos) means the cosine of the direction (angle) of measurement of light intensity, wherein the unit of the angle is degree)(°.

Incidentally, the thickness of the sheet-shaped sample used in the measurement of diffusion degree (D) is ordinarily 0.3 mm including the case of the above-mentioned Patent Literature 1. However, light-diffusing property can be measured at a higher sensitivity and the change of diffusion degree (D) is larger, as the thickness of the sheet-shaped sample is larger. Accordingly, in the present invention, 0.5 mm is adopted as the thickness of the sheet-shaped sample. In the cured body of present dental restorative material, the diffusion degree (D) can be set at ordinarily 5 or larger, preferably 10 or larger, particularly preferably 20 to 40.

Hereinafter, the present invention is described specifically by way of Examples and Comparative Examples. However, the present invention is in no way restricted thereby.

The abbreviations of the polymerizable matrixes, organic-inorganic composite fillers, inorganic fillers, etc. all used in the following Examples and Comparative examples, are shown below.

[Polymerizable Matrixes]

A-1

A uniform solution (a cured body thereof had a refractive index of 1.555 at 32° C.) obtained by dissolving the following materials in a dark place:

8 g of 2,2-bis(4-methacryloyloxypolyethoxyphenyl)propane (a cured body thereof had a refractive index of 1.567 at 32° C.), 1 g of triethylene glycol dimethacrylate (a cured body thereof had a refractive index of 1.509 at 32° C.), 1 g of 1,6-bis(methacrylethyloxycarbonylamino)trimethylhexane (a cured body thereof had a refractive index of 1.510 at 32° C.),
0.02 g of camphorquinone,
0.02 g of ethyl p-dimethylaminobenzoate,
0.01 g of hydroquinone monomethyl ether, and
0.002 g of bidutylhydroxytoluene.

A-2

A uniform solution (a cured body thereof had a refractive index of 1.543 at 32° C.) obtained by dissolving the following materials in a dark place:
6 g of 2,2-bis(4-methacryloyloxypolyethoxyphenyl)propane (a cured body thereof had a refractive index of 1.567 at 32° C.),
2 g of triethylene glycol dimethacrylate (a cured body thereof had a refractive index of 1.509 at 32° C.),
2 g of 1,6-bis(methacrylethyloxycarbonylamino)trimethylhexane (a cured body thereof had a refractive index of 1.510 at 32° C.),
0.02 g of camphorquinone,
0.02 g of ethyl p-dimethylaminobenzoate,
0.01 g of hydroquinone monomethyl ether, and
0.002 g of dibutylhydroxytoluene.

A-3

A uniform solution (a cured body thereof had a refractive index of 1.543 at 32° C.) obtained by dissolving the following materials in a dark place:
3 g of 2,2-bis(4-methacryloyloxypolyethoxyphenyl)propane (a cured body thereof had a refractive index of 1.567 at 32° C.),
3 g of triethylene glycol dimethacrylate (a cured body thereof had a refractive index of 1.509 at 32° C.),
4 g of 1,6-bis(methacrylethyloxycarbonylamino)trimethylhexane (a cured body thereof had a refractive index of 1.510 at 32° C.),
0.02 g of camphorquinone,
0.02 g of ethyl p-dimethylaminobenzoate,
0.01 g of hydroquinone monomethyl ether, and
0.002 g of dibutylhydroxytoluene.

A-4

A uniform solution (a cured body thereof had a refractive index of 1.543 at 32° C.) obtained by dissolving the following materials in a dark place:
4.5 g of 2,2-bis(4-methacryloyloxypolyethoxyphenyl)propane (a cured body thereof had a refractive index of 1.567 at 32° C.),
3 g of triethylene glycol dimethacrylate (a cured body thereof had a refractive index of 1.509 at 32° C.),
2.5 g of 1,6-bis(methacrylethyloxycarbonylamino)trimethylhexane (a cured body thereof had a refractive index of 1.510 at 32° C.),
0.02 g of camphorquinone,
0.02 g of ethyl p-dimethylaminobenzoate,
0.01 g of hydroquinone monomethyl ether, and
0.002 g of dibutylhydroxytoluene.

[Organic-Inorganic Composite Fillers]

B-1

There were kneaded:
an inorganic fine filler obtained by subjecting 80 g of spherical silica-zirconia [average particle diameter: 0.2 µm, refractive index at 32° C.: 1.521, coefficient of variation: 9%] to a surface treatment with γ-methacryloyloxypropyltrimethoxysilane, and
a matrix monomer obtained by mixing 6 g of triethylene glycol dimethacrylate (a cured body thereof had a refractive index of 1.509 at 32° C.), 14 g of 1,6-bis(methacrylethyloxycarbonylamino)trimethylhexane (a cured body thereof had a refractive index of 1.510 at 32° C.) (these two compounds were polymerizable monomers), and 0.06 g of azobisisobutyronitrile as a polymerization initiator, to obtain a paste. The paste was heated at 100° C. for 1 hour under a nitrogen pressure to give rise to polymerization and curing. The polymer obtained was ground for 30 minutes using a vibration ball mill to obtain an organic-inorganic composite filler B-1 [average particle diameter: 11.5 µm, refractive index at 32° C.: 1.516, coefficient of variation: 53%].

B-2

There was produced an organic-inorganic composite filler B-2 [average particle diameter: 12.2 µm, refractive index at 32° C.: 1.528, coefficient of variation: 56%] in the same manner as in B-1 except that the polymerizable monomers mixed with the inorganic fine filler were changed to 0.9 g of 2,2-bis(4-methacryloyloxypolyethoxyphenyl)propane (a polymer thereof had a refractive index of 1.567 at 32° C.), 0.5 g of triethylene glycol dimethacrylate (a polymer thereof had a refractive index of 1.509 at 32° C.), and 0.6 g of 1,6-bis(methacrylethyloxycarbonylamino)trimethylhexane (a polymer thereof had a refractive index of 1.510 at 32° C.)

B-3

There was produced an organic-inorganic composite filler B-3 [average particle diameter: 6.3 µm, refractive index at 32° C.: 1.516, coefficient of variation: 61%] in the same manner as in B-1 except that the grinding time using a vibration ball mill was changed from 30 minutes to 60 minutes.

B-4

There was produced an organic-inorganic composite filler B-4 [average particle diameter: 9.1 µm, refractive index at 32° C.: 1.516, coefficient of variation: 59%] in the same manner as in B-1 except that the grinding time using a vibration ball mill was changed from 30 minutes to 45 minutes.

B-5

There was produced an organic-inorganic composite filler B-5 [average particle diameter: 18.7 µm, refractive index at 32° C.: 1.516, coefficient of variation: 48%] in the same manner as in B-1 except that the grinding time using a vibration ball mill was changed from 30 minutes to 20 minutes.

B-6

There was produced an organic-inorganic composite filler B-6 [average particle diameter: 32.1 µm, refractive index at 32° C.: 1.516, coefficient of variation: 45%] in the same manner as in B-1 except that the grinding time using a vibration ball mill was changed from 30 minutes to 15 minutes.

B-7

There was produced an organic-inorganic composite filler B-7 [average particle diameter: 12.2 µm, refractive index: 1.533, coefficient of variation: 52%] in the same manner as in B-1 except that the polymerizable monomers mixed with the inorganic fine filler were changed to 1.2 g of 2,2-bis(4-methacryloyloxypolyethoxyphenyl)propane (a polymer thereof had a refractive index of 1.567 at 32° C.), 0.4 g of triethylene glycol dimethacrylate (a polymer thereof had a refractive index of 1.509 at 32° C.), and 0.4 g of 1,6-bis(methacrylethyloxycarbonylamino)trimethylhexane (a polymer thereof had a refractive index of 1.510 at 32° C.)

B-8

There was produced an organic-inorganic composite filler B-8 [average particle diameter: 3.4 µm, refractive index at 32° C.: 1.516, coefficient of variation: 75%] in the same manner as in B-1 except that the grinding time using a vibration ball mill was changed from 30 minutes to 100 minutes.

B-9

There was produced an organic-inorganic composite filler B-9 [average particle diameter: 68.7 µm, refractive index at 32° C.: 1.516, coefficient of variation: 39%] in the same manner as in B-1 except that the grinding time using a vibration ball mill was changed from 30 minutes to 5 minutes.

B-10

100 g of spherical silica-zirconia (average particle diameter: 0.2 µm; refractive index at 32° C.: 1.521; coefficient of variation: 9%) was added in 200 g of water, and the inorganic fine filler was dispersed in the water using a circulation type grinder (SC mill) to obtain a dispersion. Then, 4 g of γ-methacryloyloxypropyltrimethoxysilane and 0.003 g of acetic acid were added to 80 g of water, followed by stirring for 1 hour and 30 minutes to obtain a uniform solution of pH 4. This solution was added to the above-prepared dispersion of inorganic fine filler, followed by stirring to obtain a uniformly mixed solution. Thereafter, the mixed solution, while being mixed mildly, was fed to a spray drier (Spray Drier TSR-2W, manufactured by Sakamoto Giken K.K.) and spray-dried. This spray drier is an apparatus for feeding the mixed solution onto a disc rotating at a high speed and spray-drying the solution with a centrifugal force. The rotational speed of the disc was 20,000 rµm and the temperature of air was 200° C.

Then, the spray-dried inorganic fine filler was vacuum-dried at 60° C. for 18 hours to obtain 71 g of agglomerated particles of inorganic fine filler. The pores formed by the agglomeration gaps between the agglomerated particles had a pore volume of 0.18 cm$^3$/g and an average pore diameter of 38 nm. The agglomerated particles had an average particle diameter of 40.0 µm.

Incidentally, the pore volume of the pores formed by the agglomeration gaps between agglomerated particles was measured by using a mercury porosimeter (Pore Master, manufactured by Quantachrome). First, 0.2 g of agglomerated particles or an organic-inorganic composite filler was placed in a measurement cell, and the pore volume distribution of the agglomerated particles or the like was measured. The pore volumes in the pore diameter range of 1 to 500 nm of the pore volume distribution obtained were integrated and determined as pore volume. Also, for the pores of the above pore diameter range, the median pore diameter was determined from the pore volume distribution and taken as average pore diameter of agglomeration gaps.

Next, there were mixed 0.3 g of triethylene glycol dimethacrylate (a polymer thereof had a refractive index of 1.509 at 32° C.), 0.7 g of 1,6-bis(methacrylethyloxycarbonylamino)trimethylhexane (a polymer thereof had a refractive index of 1.510 at 32° C.) (these two compounds were each used as a polymerizable monomer), 0.003 g of azobisisobutyronitrile, and 5.0 g of ethanol as an organic solvent, to prepare a polymerizable monomer solution. In this polymerizable monomer solution were immersed 10.0 g of the above-obtained agglomerated inorganic particles, followed by sufficient stirring. After the mixture was confirmed to have become slurry by stirring, the slurry was allowed to stand for 1 hour.

While the above mixture was stirred by a rotary evaporator, the organic solvent was removed for 1 hour under the conditions of vacuum of 10 hPa and heating at 40° C. (a hot water bath was used), to obtain a non-sticky powder.

While the powder was stirred using a rotary evaporator, the powder was heated for 1 hour under the conditions of vacuum of 10 hPa and heating at 100° C. (an oil bath was used), to polymerize and cure the polymerizable monomers contained in the powder and obtain 8.5 g of an organic-inorganic composite filler. The pores formed by the agglomeration gaps of this organic-inorganic composite filler had a pore volume of 0.07 cm$^3$/g and an average pore diameter of 21 nm. The organic-inorganic composite filler had an average particle diameter of 13.6 µm, a refractive index of 1.516 at 32° C. and a coefficient of variation of 57%.

[Third Component Inorganic Filler]

C-1: An inorganic filler obtained by subjecting irregular-shaped silica-zirconia to a surface treatment with γ-methacryloyloxypropyltrimethoxysilane; average particle diameter: 1.5 µm, refractive index: 1.535 at 32° C., coefficient of variation: 34%.

C-2: An inorganic filler obtained by subjecting irregular-shaped shape silica-zirconia to a surface treatment with γ-methacryloyloxypropyltrimethoxysilane; average particle diameter: 1.6 µm, refractive index: 1.526 at 32° C., coefficient of variation: 33%.

C-3: An inorganic filler obtained by subjecting irregular-shaped shape silica-zirconia to a surface treatment with γ-methacryloyloxypropyltrimethoxysilane; average particle diameter: 1.5 µm, refractive index: 1.545 at 32° C., coefficient of variation: 36%.

C-4: An inorganic filler obtained by subjecting spherical silica-barium oxide to a surface treatment with γ-methacryloyloxypropyltrimethoxysilane; average particle diameter: 1.4 µm, refractive index: 1.570 at 32° C., coefficient of variation: 35%.

C-5: An inorganic filler obtained by subjecting irregular-shaped shape silica-zirconia to a surface treatment with γ-methacryloyloxypropyltrimethoxysilane; average particle diameter: 1.1 µm, refractive index: 1.535 at 32° C., coefficient of variation: 34%.

C-6: An inorganic filler obtained by subjecting irregular-shaped shape silica-zirconia to a surface treatment with γ-methacryloyloxypropyltrimethoxysilane; average particle diameter: 4.2 µm, refractive index: 1.535 at 32° C., coefficient of variation: 29%.

C-7: An inorganic filler obtained by subjecting irregular-shaped shape silica-zirconia to a surface treatment with γ-methacryloyloxypropyltrimethoxysilane; average particle diameter: 0.7 µm, refractive index: 1.537 at 32° C., coefficient of variation: 38%.

C-8: An inorganic filler obtained by subjecting irregular-shaped shape silica-zirconia to a surface treatment with γ-methacryloyloxypropyltrimethoxysilane; average particle diameter: 0.2 µm, refractive index: 1.537 at 32° C., coefficient of variation: 46%.

C-9: An inorganic filler obtained by subjecting irregular-shaped shape silica-zirconia to a surface treatment with γ-methacryloyloxypropyltrimethoxysilane; average particle diameter: 7.3 µm, refractive index: 1.536 at 32° C., coefficient of variation: 33%.

[Other Inorganic Filler]

D-1: An inorganic filler obtained by subjecting spherical silica-zirconia (average particle diameter: 0.2 µm, refractive index: 1.521 at 32° C., coefficient of variation: 9%) to a surface treatment with γ-methacryloyloxypropyltrimethoxysilane.

The properties of the above fillers, etc. and the properties of the dental restorative materials in the following Examples and Comparative Examples were measured by the following methods.

(1) Average Particle Diameters and Coefficients of Variation of Inorganic Fine Filler (Dispersed in Organic-Inorganic Composite Filler) and Third Component Inorganic Filler The photograph of a third component inorganic filler or an organic-inorganic composite filler was taken using a scanning electron microscope (XL-30S FEG manufactured by PHILIPS), at a magnification of 5,000 to 100,000. The photograph was treated using an image-processing soft (IP-1000 PC, manufactured by ASAHI KASEI ENGINEERING CORPO- RATION) to determine the circle-equivalent diameter (particle diameter), maximum length, minimum width and particle number of primary particles in a unit visual field. The particle number was 100 or larger and automatically determined depending upon the measurement conditions of the microscope. The average particle diameter and coefficient of variation of primary particles were calculated using the following formulas.

$$X = \sqrt[3]{\frac{\sum_{i=1}^{n} X_i^3}{n}} \text{ (average volume diameter)}$$ [Mathematical expression 2]

Average particle diameter.

$n$: Number of observed particles
$x_i$: Particle diameter of $i$th particle $$CV = (SD/X) \times 100(\%)$$ [Mathematical expression 3]

$SD$ is a standard deviation and
$X$ is an arithmetic mean diameter.

(2) Measurement of Average Particle Diameter of Organic-Inorganic Composite Filler There was used a particle size analyzer (LS 230 manufactured by BECKMAN COULTER CO., LTD.) based on the laser scattering type particle size distribution measurement method. 0.1 g of an organic-inorganic composite filler was dispersed in 10 ml of ethanol and the dispersion was subjected to a dispersion treatment using an ultrasonic wave, for 5 minutes. Immediately, average particle diameter was measured using the particle size analyzer. Incidentally, as the average particle diameter, median diameter in a particle size distribution on volume basis was adopted.

(3) Measurement of Refractive Indices of Organic-Inorganic Composite Filler and Third Component Inorganic Filler Refractive index at 32° C. was measured using an Abbe's refractometer manufactured by Atago Co., Ltd. The refractive index of each filler was measured by an immersion method. That is, a filler was dispersed in ethanol; 1-bromonaphthalin was slowly dropped into the resulting dispersion; the refractive index of the dispersion when the boundary between the filler and the liquid could not be confirmed visually, was taken as the refractive index of the filler.

(4) Color Conformability

In each of three kinds of artificial teeth having different color, i.e. SURPASS ANTERIOR TOOTH A2 SHADE, A3 SHADE AND C3 SHADE (manufactured by GC CORPORATION) was formed a semi-spherical cavity of 5 mm in diameter using a drill. Then, each of the dental restorative materials produced in Examples and Comparative Examples (each material had been colored in a color corresponding to that of SURPASS ANTERIOR TOOTH A2 SHADE) was filled into the cavity of each artificial tooth. Sufficient photopolymerization was allowed to take place to cure each dental restorative material to obtain each cured body. The color conformability of each cured body was rated visually. The criteria for rating is as follows.

VG: The boundary between artificial tooth and cured body is unrecognizable in any artificial tooth.
G: The boundary between artificial tooth and cured body is unrecognizable in two kinds of artificial teeth, but is recognizable in other one kind of artificial tooth.
NG: The boundary between artificial tooth and cured body is unrecognizable in one kind of artificial tooth, but is recognizable in other two kinds of artificial teeth.
X: The boundary between artificial tooth and cured body is recognizable in any artificial tooth.

(5) Diffusion Degree

A dental restorative material was filled in a mold (a sheet of 0.5 mm in thickness) having a through-hole of 30 mm in diameter at the center. Sufficient photopolymerization was allowed to take place to cure the dental restorative material to obtain a cured body. The cured body was taken out of the mold and immersed in water of 37° C. for 24 hours to obtain a specimen. The specimen was measured for light intensity distribution of transmitted light using a gonio-photometer (GP-2000 of Murakami Research Laboratory). Diffusion degree (D) was calculated using the following formula.

$$D = \{(I_{20}/\cos 20°) + (I_{70}/\cos 70°)\}/(2 \times I_0)$$

In the above formula, $I_0$, $I_{20}$ and $I_{70}$ are, when a light is applied perpendicularly to the surface of the above-obtained sheet-shaped specimen of 0.5 mm in thickness, the intensities of lights transmitted by the specimen in the directions of 0°, 20° and 70° relative to the incident direction of the light applied.

The measurement of these light intensities can be conducted easily using a gonio-photometer.

(6) Flexural Strength

A dental restorative material was filled in a mold having a square column-shaped dent of 2×2×25 mm. Sufficient photopolymerization was allowed to take place to cure the dental restorative material to obtain a cured body. The cured body was taken out of the mold and immersed in water of 37° C. for 24 hours to obtain a specimen. The specimen was set to a tester (Autograph 5000 D manufactured by Shimadzu Corporation) and measured for breaking strength in 3-point bending test, at a fulcrum-to-fulcrum distance of 20 mm and a cross-head speed of 1 mm/min.

(7) Handling Property of Dental Restorative Material

The handling property of a paste-like dental restorative material, i.e. paste property was examined based on the following criteria. This test is to examine the easiness of filling the dental restorative material into the cavity of tooth.

VG: Filling is very easy.
G: Tackiness and non-tackiness are adequate and filling is easy.
X: Tackiness and non-tackiness are high and filling is difficult.

(8) Surface Smoothness and Gloss

A dental restorative material was filled in a mold having a square column-shaped dent of 10 (depth)×10 (width)×2 (height) mm. Sufficient photopolymerization was allowed to take place to cure the dental restorative material to obtain a cured body. The cured body was taken out of the mold and immersed in water of 37° C. for 24 hours to obtain a specimen. The surface of this specimen was polished with a water-resistant abrasive paper No. 1500 and then finish-polished with Sof-lex Superfine (manufactured by 3M) for 1 minute. Thereafter, the surface gloss was rated visually.

VG: Good in smoothness and gloss
G: Slightly inferior in smoothness and gloss
X: Inferior in smoothness and gloss Example 1

There were mixed 10 g of A-1 (polymerizable monomer), 15 g of B-1 (organic-inorganic composite filler), and 25 g of C-1 (inorganic filler), to obtain a curable paste. The curable paste was colored into a color equivalent to artificial tooth "SURPASS ANTERIOR TOOTH A2 SHADE" (manufactured by GC Corporation), using the following pigments:

white pigment: titanium oxide (average particle diameter: 0.25 μm)
yellow pigment: Pigment Yellow 95
red pigment: Pigment Red 166
blue pigment: Pigment Blue 60 to obtain a dental restorative material.

This dental restorative material had a contrast ratio of 0.60 as measured by the following method. Also, the cured body of 0.5 mm in thickness used in the measurement of this contrast ratio showed, in a white background, L* of 71.0, a* of −0.5 and b* of 19.0. The contrast ratio is a property indicating the opaqueness of cured body.

(Measurement of Contrast Ratio)

A dental restorative material was filled in a Teflon (registered trademark)-made mold of 1.0 mm in thickness, having a disc-shaped hole of 0.5 mm in depth. A light was applied to the dental restorative material for 30 seconds using a visible light applicator for dental use, for curing. The cured body obtained was removed from the mold to obtain a cured body of 0.5 mm in thickness. The cured body was measured for Y value using a color-difference meter (1800 MKII manufactured by Tokyo Denshoku Co., Ltd.). The Y value is a value relating to the lightness of the tristimulus values of XYZ chromatic system in a black background or a white background.

The above value obtained was substituted into the following formula to obtain a contrast ratio.

$Yb(Y\text{ value in black background})/Yw(Y\text{ value in white background}) = \text{contrast ratio}$ The dental restorative material was examined for various properties. The results are shown in Table 3.

Examples 2 to 20, Comparative Examples 1 to 7

Dental restorative materials having the compositions shown in Table 1 and Table 2 were prepared in the same manner as in Example 1. Each of these dental restorative materials had been colored in a color corresponding to the artificial tooth "SURPASS ANTERIOR TOOTH A2 SHADE".

These dental restorative materials were examined for properties. The results are shown in Table 3 and Table 4.

TABLE 1

| | (A) Polymerizable monomer | | | (B) Organic-inorganic composite filler | | | |
|---|---|---|---|---|---|---|---|
| | Component | Refractive index of polymer nA | Use amount | Component | Refractive index nB | Average particle diameter (μm) | Use amount |
| Ex. 1 | A-1 | 1.555 | 20 | B-1 | 1.516 | 11.5 | 30 |
| Ex. 2 | A-1 | 1.555 | 20 | B-1 | 1.516 | 11.5 | 30 |
| Ex. 3 | A-1 | 1.555 | 20 | B-2 | 1.528 | 12.2 | 30 |
| Ex. 4 | A-1 | 1.555 | 20 | B-2 | 1.528 | 12.2 | 30 |
| Ex. 5 | A-1 | 1.555 | 20 | B-1 | 1.516 | 11.5 | 30 |
| Ex. 6 | A-2 | 1.543 | 20 | B-1 | 1.516 | 11.5 | 30 |
| Ex. 7 | A-3 | 1.528 | 20 | B-1 | 1.516 | 11.5 | 30 |
| Ex. 8 | A-1 | 1.555 | 20 | B-3 | 1.516 | 6.3 | 30 |
| Ex. 9 | A-1 | 1.555 | 20 | B-4 | 1.516 | 9.1 | 30 |
| Ex. 10 | A-1 | 1.555 | 20 | B-5 | 1.516 | 18.7 | 30 |
| Ex. 11 | A-1 | 1.555 | 20 | B-6 | 1.516 | 32.1 | 30 |
| Ex. 12 | A-1 | 1.555 | 20 | B-1 | 1.516 | 11.5 | 30 |
| Ex. 13 | A-1 | 1.555 | 20 | B-1 | 1.516 | 11.5 | 30 |
| Ex. 14 | A-1 | 1.555 | 20 | B-1 | 1.516 | 11.5 | 5 |
| Ex. 15 | A-1 | 1.555 | 20 | B-1 | 1.516 | 11.5 | 12 |
| Ex. 16 | A-1 | 1.555 | 20 | B-1 | 1.516 | 11.5 | 30 |
| Ex. 17 | A-1 | 1.555 | 20 | B-1 | 1.516 | 11.5 | 70 |
| Ex. 18 | A-1 | 1.555 | 13 | B-1 | 1.516 | 11.5 | 30 |
| Ex. 19 | A-1 | 1.555 | 45 | B-1 | 1.516 | 11.5 | 30 |
| Ex. 20 | A-1 | 1.555 | 20 | B-10 | 1.516 | 13.6 | 30 |

| | (C) Third component inorganic filler | | | Other filler | | Difference of refractive index nC − nB | Difference of refractive index nA − nC |
|---|---|---|---|---|---|---|---|
| | Component | Refractive index nC | Average particle diameter (μm) | Use amount | Component | Use amount | | |
| Ex. 1 | C-1 | 1.535 | 1.5 | 50 | — | | 0.019 | 0.020 |
| Ex. 2 | C-2 | 1.526 | 1.6 | 50 | — | | 0.010 | 0.029 |
| Ex. 3 | C-1 | 1.535 | 1.5 | 50 | — | | 0.007 | 0.020 |
| Ex. 4 | C-3 | 1.545 | 1.5 | 50 | — | | 0.017 | 0.010 |
| Ex. 5 | C-4 | 1.570 | 1.4 | 50 | — | | 0.054 | −0.015 |
| Ex. 6 | C-1 | 1.535 | 1.5 | 50 | — | | 0.019 | 0.008 |
| Ex. 7 | C-1 | 1.535 | 1.5 | 50 | — | | 0.019 | −0.007 |
| Ex. 8 | C-1 | 1.535 | 1.5 | 50 | — | | 0.019 | 0.020 |
| Ex. 9 | C-1 | 1.535 | 1.5 | 50 | — | | 0.019 | 0.020 |
| Ex. 10 | C-1 | 1.535 | 1.5 | 50 | — | | 0.019 | 0.020 |
| Ex. 11 | C-1 | 1.535 | 1.5 | 50 | — | | 0.019 | 0.020 |
| Ex. 12 | C-5 | 1.535 | 1.1 | 50 | — | | 0.019 | 0.020 |
| Ex. 13 | C-6 | 1.535 | 4.2 | 50 | — | | 0.019 | 0.020 |
| Ex. 14 | C-1 | 1.535 | 1.5 | 50 | D-1 | 25 | 0.019 | 0.020 |
| Ex. 15 | C-1 | 1.535 | 1.5 | 50 | D-1 | 18 | 0.019 | 0.020 |

TABLE 1-continued

| | | | | | | | | |
|---|---|---|---|---|---|---|---|---|
| Ex. 16 | C-1 | 1.535 | 1.5 | 10 | D-1 | 30 | 0.019 | 0.020 |
| Ex. 17 | C-1 | 1.535 | 1.5 | 10 | — | | 0.019 | 0.020 |
| Ex. 18 | C-1 | 1.535 | 1.5 | 57 | — | | 0.019 | 0.020 |
| Ex. 19 | C-1 | 1.535 | 1.5 | 25 | — | | 0.019 | 0.020 |
| Ex. 20 | C-1 | 1.535 | 1.5 | 50 | — | | 0.019 | 0.020 |

TABLE 2

| | (A) Polymerizable monomer | | (B) Organic-inorganic composite filler | | | |
|---|---|---|---|---|---|---|
| | Component | Refractive index of polymer nA | Use amount | Component | Refractive index nB | Average particle diameter (μm) | Use amount |
| Comp. Ex. 1 | A-1 | 1.555 | 20 | B-7 | 1.533 | 10.8 | 30 |
| Comp. Ex. 2 | A-4 | 1.535 | 20 | B-1 | 1.516 | 11.5 | 30 |
| Comp. Ex. 3 | A-1 | 1.555 | 20 | B-8 | 1.516 | 3.4 | 30 |
| Comp. Ex. 4 | A-1 | 1.555 | 20 | B-9 | 1.516 | 68.7 | 30 |
| Comp. Ex. 5 | A-1 | 1.555 | 20 | B-1 | 1.516 | 11.5 | 30 |
| Comp. Ex. 6 | A-1 | 1.555 | 20 | B-1 | 1.516 | 11.5 | 30 |
| Comp. Ex. 7 | A-1 | 1.555 | 20 | B-1 | 1.516 | 11.5 | 30 |

| | (C) Third component inorganic filler | | | Other filler | | Difference of refractive index nB − nA | Difference of refractive index nC − nA |
|---|---|---|---|---|---|---|---|
| | Component | Refractive index nC | Average particle diameter (μm) | Use amount | Component | Use amount | | |
| Comp. Ex. 1 | C-1 | 1.535 | 1.5 | 50 | — | | 0.002 | 0.020 |
| Comp. Ex. 2 | C-1 | 1.535 | 1.5 | 50 | — | | 0.019 | 0.000 |
| Comp. Ex. 3 | C-1 | 1.535 | 1.5 | 50 | — | | 0.019 | 0.020 |
| Comp. Ex. 4 | C-1 | 1.535 | 1.5 | 50 | — | | 0.019 | 0.020 |
| Comp. Ex. 5 | C-7 | 1.537 | 0.7 | 50 | — | | 0.021 | 0.018 |
| Comp. Ex. 6 | C-8 | 1.537 | 0.2 | 50 | — | | 0.021 | 0.018 |
| Comp. Ex. 7 | C-9 | 1.536 | 7.3 | 50 | — | | 0.020 | 0.019 |

TABLE 3

| | Color conformability | Diffusibility (%) | Flexural strength (Mpa) | Handling property of dental restorative material | Surface smoothness and gloss |
|---|---|---|---|---|---|
| Ex. 1 | VG | 27.3 | 121 | G | G |
| Ex. 2 | VG | 25.8 | 123 | G | G |
| Ex. 3 | G | 14.2 | 119 | G | G |
| Ex. 4 | VG | 25.4 | 120 | G | G |
| Ex. 5 | G | 43.7 | 124 | G | G |
| Ex. 6 | G | 19.8 | 118 | G | G |
| Ex. 7 | G | 15.3 | 120 | G | G |
| Ex. 8 | o | 18.9 | 126 | G | G |
| Ex. 9 | VG | 28.9 | 128 | G | G |
| Ex. 10 | VG | 26.8 | 116 | G | G |
| Ex. 11 | G | 18.7 | 113 | G | G |
| Ex. 12 | G | 16.8 | 118 | G | G |
| Ex. 13 | G | 19.4 | 133 | G | G |
| Ex. 14 | G | 15.1 | 141 | G | G |
| Ex. 15 | VG | 23.1 | 138 | G | G |
| Ex. 16 | G | 16.4 | 126 | G | G |
| Ex. 17 | VG | 30.2 | 92 | NG | G |
| Ex. 18 | G | 19.7 | 133 | G | G |
| Ex. 19 | G | 17.3 | 97 | G | G |
| Ex. 20 | VG | 28.0 | 176 | G | G |

TABLE 4

|  | Color conformability | Diffusibility (%) | Flexural strength (Mpa) | Handling property of dental restorative material | Surface smoothness and gloss |
|---|---|---|---|---|---|
| Comp. Ex. 1 | NG | 7.9 | 124 | G | G |
| Comp. Ex. 2 | NG | 9.8 | 129 | G | G |
| Comp. Ex. 3 | X | 4.7 | 119 | G | G |
| Comp. Ex. 4 | NG | 9.0 | 143 | NG | G |
| Comp. Ex. 5 | NG | 8.8 | 122 | G | G |
| Comp. Ex. 6 | NG | 9.1 | 126 | G | G |
| Comp. Ex. 7 | NG | 9.4 | 130 | NG | X |

The invention claimed is:

1. A dental restorative material comprising
10 to 50 mass % of (A) a polymerizable monomer, relative to the total mass of (A), (B) and (C),
5 to 80 mass % of (B) an organic-inorganic composite filler having an average particle diameter of 5.0 to 50 μm, which organic-inorganic composite filler comprises an inorganic fine filler having an average particle diameter of 1 μm or smaller and an organic matrix dispersing the inorganic fine filler therein, and the mass % of (B) is relative to the total mass of (A), (B) and (C), and
10 to 60 mass % of (C) a third component inorganic filler having an average particle diameter of 1.1 to 5.0 μm, and the mass % of (C) is relative to the total mass of (A), (B) and (C),
wherein
the value [nC−nB] of the difference between the refractive index [nC] of the inorganic filler (C) at 32° C. and the refractive index [nB] of the organic-inorganic composite filler (B) at 32° C. is 0.01 to 0.03, and
the absolute value |nA−nC| of the difference between the refractive index [nA] of the cured body of the polymerizable monomer (A) at 32° C. and the refractive index [nC] of the inorganic filler (C) at 32° C. is 0.005 to 0.05, and
when cured, a diffusion degree (D) is 10 or larger, said diffusion degree being represented by the formula:

$$D=\{(I_{20}/\cos 20°)+(I_{70}/\cos 70°)\}/(2\times I_0),$$

wherein $I_0$, $I_{20}$ and $I_{70}$ are the intensities of light transmitted by a 0.5 mm thick sheet-shaped sample obtained by curing the dental restorative material, in the directions of 0°, 20° and 70°, respectively, relative to the incident direction of the light applied perpendicularly to the surface of the sample.

2. The dental restorative material according to claim 1, wherein material of the inorganic fine filler is silica-zirconia, silica-titania, silica-titania-barium oxide, or quartz.

3. The dental restorative material according to claim 1, wherein material of the third component inorganic filler is silica-zirconia, silica-titania, silica-titania-barium oxide, or quartz.

4. The dental restorative material according to claim 1, which further comprises a polymerization initiator.

* * * * *